(12) United States Patent
Takao et al.

(10) Patent No.: US 7,189,320 B2
(45) Date of Patent: Mar. 13, 2007

(54) PUMP, PUMP FOR LIQUID CHROMATOGRAPHY, AND LIQUID CHROMATOGRAPHY APPARATUS

(75) Inventors: Kunihiko Takao, Tsuchiura (JP); Hironori Kaji, Hitachinaka (JP); Masahito Ito, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 245 days.

(21) Appl. No.: 10/902,039

(22) Filed: Jul. 30, 2004

(65) Prior Publication Data
US 2005/0061722 A1   Mar. 24, 2005

(30) Foreign Application Priority Data
Sep. 18, 2003  (JP)  ............................ 2003-326806

(51) Int. Cl.
    *B01D 15/08*   (2006.01)
(52) U.S. Cl. .................. 210/198.2; 210/101; 210/656; 417/44.2; 417/245; 417/254; 417/265; 417/426
(58) Field of Classification Search .............. 210/656, 210/659, 101, 198.2; 417/44.2, 243, 254, 417/265, 426
    See application file for complete search history.

(56) References Cited

U.S. PATENT DOCUMENTS

| | | | | |
|---|---|---|---|---|
| 4,958,610 | A * | 9/1990 | Yamamoto et al. | 123/478 |
| 5,637,208 | A * | 6/1997 | Dourdeville | 210/90 |
| 5,897,781 | A * | 4/1999 | Dourdeville | 210/656 |
| 6,099,724 | A * | 8/2000 | Dourdeville | 210/198.2 |
| 6,129,840 | A * | 10/2000 | Kitaoka | 210/198.2 |
| 6,610,201 | B2 * | 8/2003 | Dourdeville | 210/198.2 |
| 6,923,916 | B1 * | 8/2005 | Hiraku et al. | 210/656 |
| 7,063,513 | B2 * | 6/2006 | Hiraku et al. | 417/245 |
| 7,063,785 | B2 * | 6/2006 | Hiraku et al. | 210/198.2 |
| 2002/0017484 | A1 * | 2/2002 | Dourdeville | 210/198.2 |
| 2002/0155010 | A1 * | 10/2002 | Karp et al. | 417/413.2 |
| 2003/0062026 | A1 * | 4/2003 | Boecking | 123/446 |
| 2003/0106533 | A1 * | 6/2003 | Crofts et al. | 123/446 |
| 2004/0164013 | A1 * | 8/2004 | Takao et al. | 210/198.2 |
| 2005/0095145 | A1 * | 5/2005 | Hiraku et al. | 417/254 |

FOREIGN PATENT DOCUMENTS

| | | |
|---|---|---|
| JP | 63-36668 | 3/1988 |
| JP | 63-075375 | 5/1988 |

* cited by examiner

*Primary Examiner*—Ernest G. Therkorn
(74) *Attorney, Agent, or Firm*—Antonelli, Terry, Stout and Kraus, LLP.

(57) ABSTRACT

The invention provides a pump for liquid chromatography excellent in feeding liquid stably at an extremely low flow rate and in discharging bubbles at startup.

In a pump for liquid chromatography including a cylinder and a plunger that reciprocates in the cylinder to suck and discharge fluid, the pump further includes a large-flow-rate pump that feeds liquid by the plunger, a small-flow-rate pump that feeds the liquid by the plunger, motion conversion means that converts the rotational motion of a motor to a reciprocating motion, an actuator that directly drives the plunger, and a drive part that drives the actuator, and selectively switches means for driving the plunger.

15 Claims, 8 Drawing Sheets

PUMP, PUMP FOR LIQUID CHROMATOGRAPHY, AND LIQUID CHROMATOGRAPHY APPARATUS

CLAIM OF PRIORITY

The present application claims priority from Japanese application serial JP 2003-326806 filed on Sep. 18, 2003, the content of which is hereby incorporated by reference into this application.

FIELD OF THE INVENTION

The present invention relates to a pump excellent in feeding liquid stably at an extremely low flow rate and in discharging bubbles at startup. Particularly, the invention relates to a pump for liquid chromatography excellent in feeding liquid stably at an extremely low flow rate and in discharging bubbles at startup.

BACKGROUND OF THE INVENTION

A conventional pump for liquid chromatography generally has a construction in which eluate is sucked and discharged by a plunger reciprocating in a cylinder and a construction has been known in which a first plunger and a second plunger are independently driven by a motor to reduce a pulsating flow rate by driving both of the plungers cooperatively. One example of this construction is disclosed, for example, in a patent document 1 described below.

In this conventional technology, while a first plunger reciprocates one time, a second plunger also reciprocates one time to correct a pulsating flow rate caused by the suction of the first plunger by the operation of the second plunger. That is, the first plunger determines a liquid flow rate and the second plunger is used for correcting the pulsating flow rate caused by the first plunger.

[Patent document 1] Japanese Patent Laid-Open No. S63 (1988)-75375

However, in the above-described conventional pump for liquid chromatography, in a case where in order to feed liquid at an extremely low flow rate, the speed reduction ratio of a motor is increased to decrease the speed of the plunger or the diameter or stroke of the plunger is decreased, conversely, the liquid can not be sent at a large flow rate. For this reason, this pump presents a problem that it takes much time to fill eluate into the passage of a measurement system on the downstream side of the pump and a problem that bubbles remaining in the pump can not be easily discharged. When the bubbles can not be discharged, even if the plunger reciprocates, the plunger only compresses or expands the bubbles and cannot discharge the liquid. Therefore, there is presented a problem that this pump is not appropriate for constructing a pump used for an extremely low flow rate.

SUMMARY OF THE INVENTION

The first object of the present invention is to provide a pump suitable for feeding liquid at an extremely low flow rate, in particular, a pump for liquid chromatography. Moreover, the second object of the invention is to provide a pump capable of completing filling eluate or discharging bubbles at the startup of test in a short time, in particular, a pump for liquid chromatography.

To achieve the first object, a pump in accordance with the present invention includes a cylinder and a plunger that reciprocates in the cylinder and sucks and discharges fluid, and further includes an actuator that directly drives the plunger.

Further, a pump in accordance with the present invention includes a cylinder and a plunger that reciprocates in the cylinder and sucks and discharges fluid, and further includes motion conversion means that converts the rotational motion of a motor to a reciprocating motion, an actuator that directly drives the plunger, and a drive part that drives the actuator, and selectively switches means for driving the plunger. At this time, it is recommended that the actuator has a function for detecting load applied to the plunger. Alternatively, it is recommended that the means for driving the plunger is selectively switched according to the flow rate of liquid of the pump.

The pump in accordance with the invention is useful for a pump for liquid chromatography.

Moreover, to achieve the second object, a pump for liquid chromatography is provided with a drain valve on the downstream side of a second pump and when a test is started, the drain valve is opened and a first pump feeds liquid at a large flow rate to discharge bubbles remaining in a passage and at the same time fills the liquid into a downstream passage and thereafter the drain valve is closed and the second pump feeds the liquid at a low flow rate.

The pump for liquid chromatography is particularly effective for a flow rate of liquid ranging from 0.1 nL/min to 50 µL/min.

According to the invention, the pump includes motion conversion means that converts the rotational motion of a motor to a reciprocating motion and an actuator that directly drives the plunger, and can selectively switch means for driving the plunger. Hence, the invention can provide a pump for liquid chromatography suitable for decreasing the flow rate of liquid.

Moreover, the invention is constructed in such a way that a small pump feeds eluate at an extremely low flow rate and that a large pump fills the eluate and discharges bubbles at the startup of test. Hence, the invention can provide a pump for liquid chromatography that can complete filling the eluate and discharging bubbles at the startup of test in a short time.

DETAILED DESCRIPTION OF THE PREFERRED EMBODIMENTS

The embodiments of the invention will be described with reference to the drawings.

Figure 1:
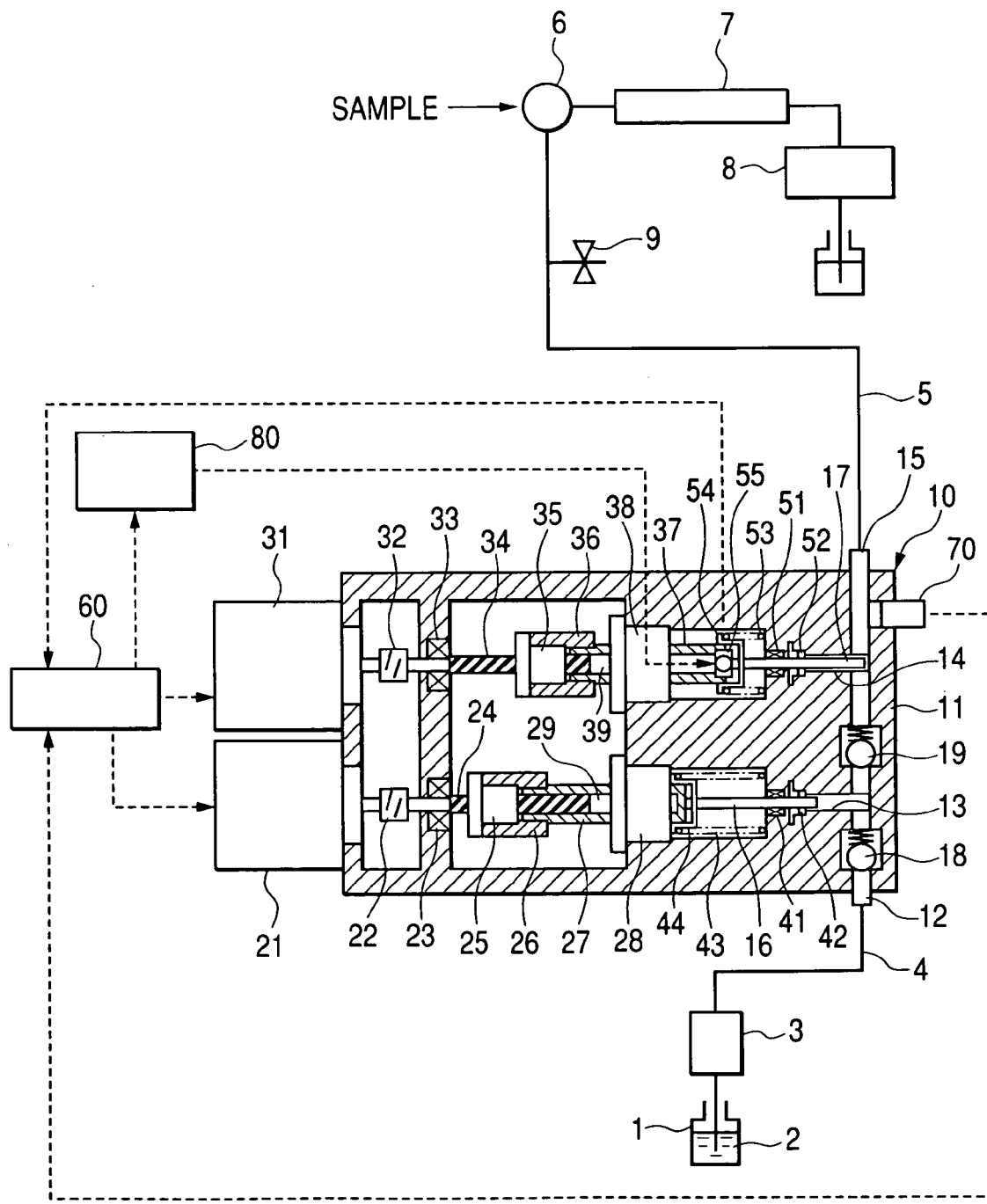
FIG. 1 is a hydraulic circuit to show the general construction of a system for feeding liquid of an object to which a pump for liquid chromatography of the invention is applied.
Figure 2:
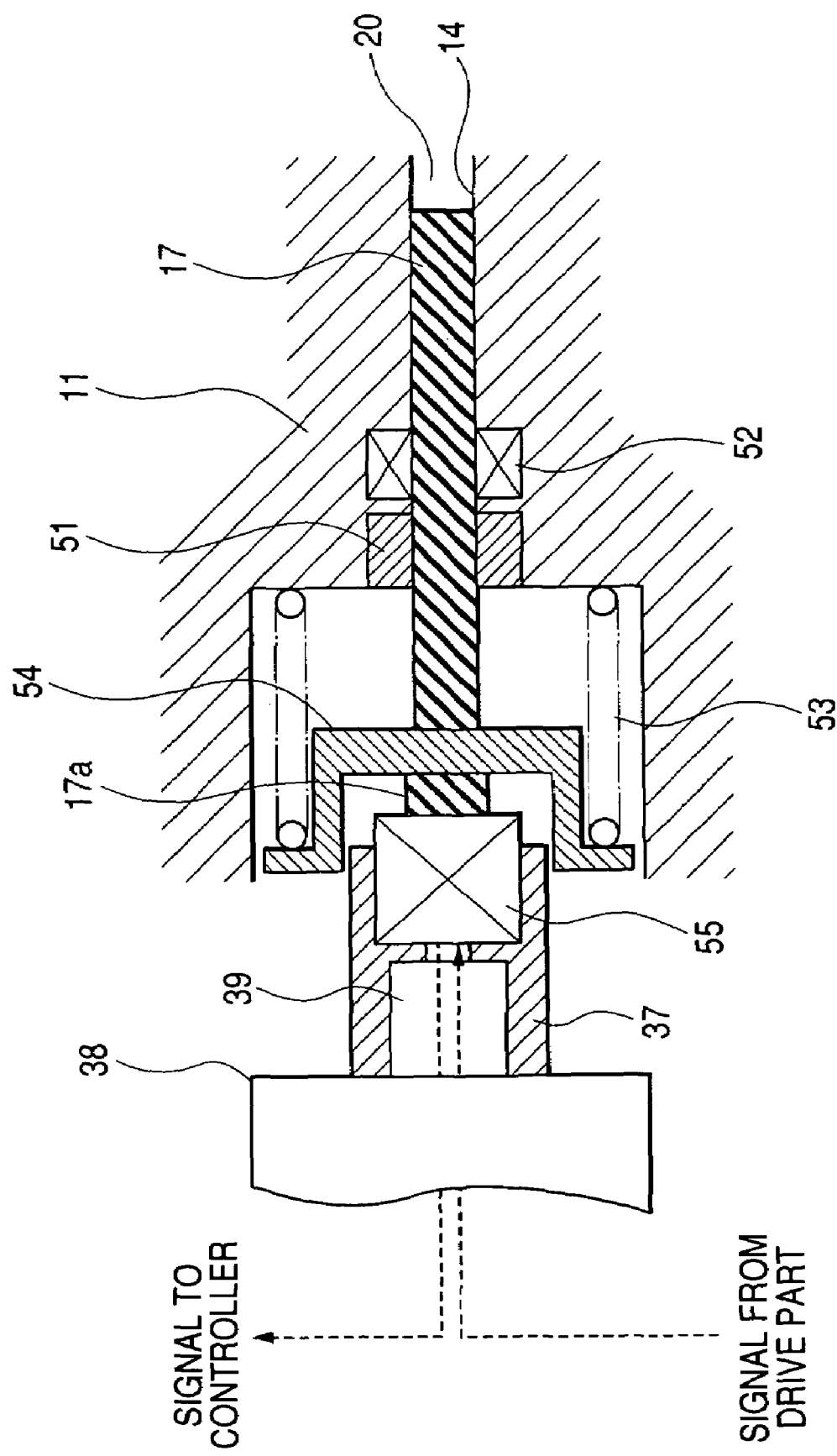
FIG. 2 is an enlarged sectional view to show the schematic structure of a pump body of the pump for liquid chromatography of the invention.
Figure 3:
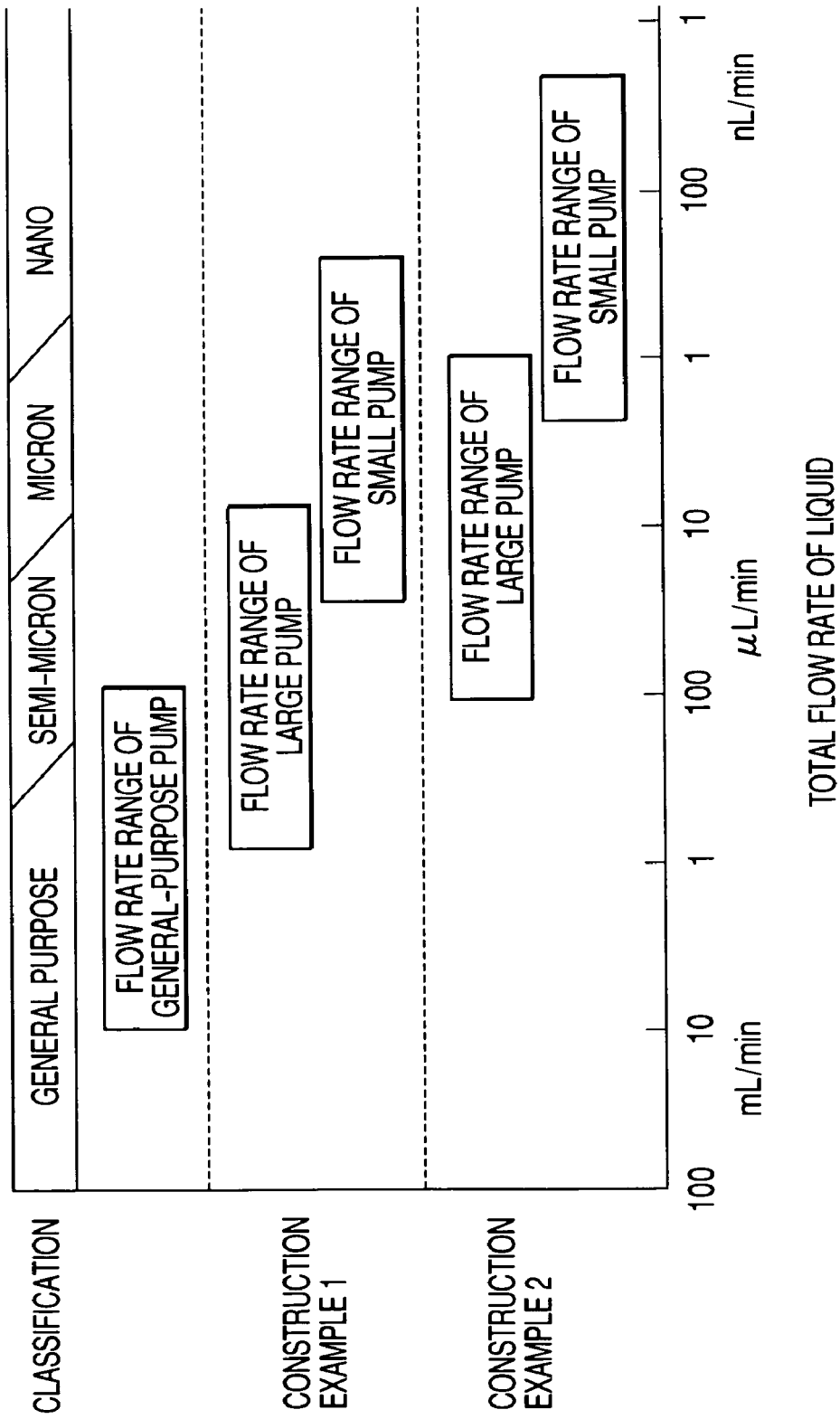
FIG. 3 is a chart to show the flow rate range of the pump for liquid chromatography of the invention.
Figure 4:
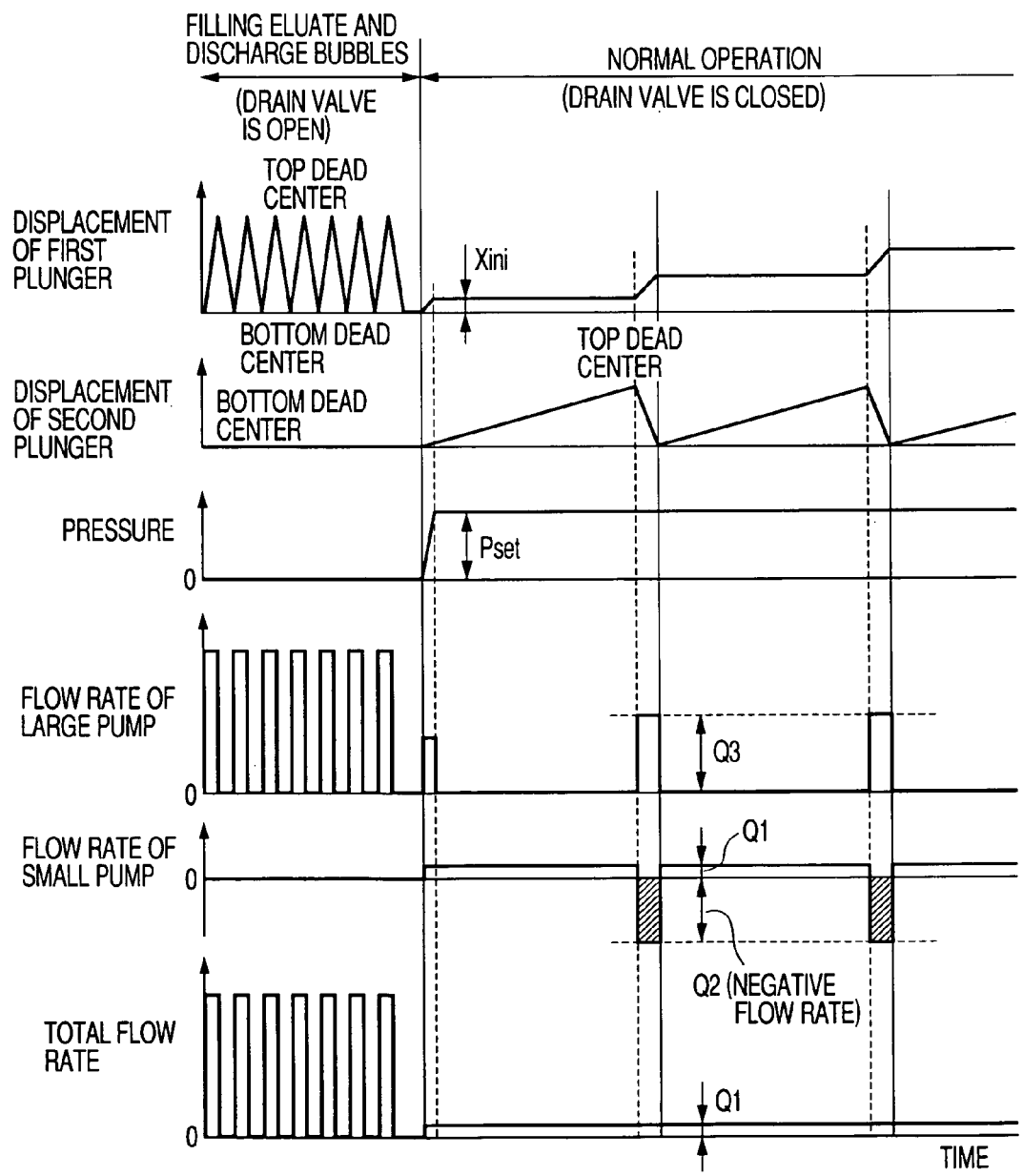
FIG. 4 is a chart to show one example of a method for driving the pump for liquid chromatography of the invention.

FIG. 1 is the hydraulic circuit to show the general construction of a system for feeding liquid of liquid chromatography to which a pump for liquid chromatography of the invention is applied. FIG. 2 is an enlarged sectional view to show the schematic structure of a pump body of the pump for liquid chromatography of the invention. FIG. 3 is a chart to show the flow rate range of the pump. FIG. 4 is a chart to show one example of a method for driving the pump for liquid chromatography.

In FIG. 1 and FIG. 2, a system for feeding liquid has a pump 10 used for liquid chromatography that sucks and pressurizes eluate 2 in an eluate storing container 1 via a degasser 3 and a suction piping 4; an injector 6 that discharges the eluate from the pump 10 used for liquid chromatography and has a sample to be analyzed injected thereto via a discharge piping 5; a column 7 filled with fine silica gel grains; a detector 8 for analyzing components for each separated component; a drain valve 9 connected to the discharge piping 5; a controller 60 for outputting a drive signal to motors 21 and 31 for driving the pump; a pressure sensor 70 that is provided in the pump 10 used for liquid chromatography and detects pressure and outputs a detection signal to the controller 60; and a drive section 80 that drives an actuator that is provided in the pump and will be described below.

The pump 10 used for liquid chromatography is constructed of a pump body 11 and the motors 21 and 31. In the pump body 11 are formed a suction passage 12, a first cylinder 13, a second cylinder 14, and a discharge passage 15. The first cylinder 13 and the second cylinder 14 hold a first plunger 16 and a second plunger 17 by bearings 41 and 51 in such a way the first plunger 16 and the second plunger 17 can slide, respectively. The suction passage 12 is provided with a suction valve 18 and a middle passage for making the first cylinder 13 communicate with the second cylinder 14 is provided with a discharge valve 19. Each of the suction valve 18 and the discharge valve 19 is a check valve that is held in one direction by a spring to limit a direction in which the eluate flows. That is, the suction valve 18 is biased by a spring such that it is opened against a spring force when a first pump having the first cylinder 13 is in a suction stroke and the discharge pump 19 is biased by a spring such that it is opened against a spring force when the first pump is in a discharge stroke.

In the pump body 11 are mounted the motors 21 and 31. At the ends of rotary shafts of the motors 21 and 31, ball screws 24, 34 are rotatably supported by bearings 23, 33 via couplings 22, 32, respectively. The nuts 25, 35 of the ball screws 24, 34 are connected to the motor side ends of ball spline shafts 27, 37 by couplings 26, 36, respectively.

The ball spline shafts 27, 37 are supported by spline outer cylinders 28, 38 fixed to the pump body 11, respectively. The ball spline is a direct-acting system in which balls mounted in the spline outer cylinder 28 (38) move linearly and smoothly in the rolling grooves of the spline shaft 27 (37) subjected to precision grinding and can transmit torque. Moreover, in the ball spline shafts 27, 37 are respectively formed hollow spaces 29, 39 having inside diameter slightly larger than the outside diameters of the ball screws 24, 34, and the ball screws 24, 34 can freely come into or go out of the hollow spaces 29, 39.

As shown in detail in FIG. 2, the second plunger 17 is slidably supported by the bearing 51 in the second cylinder 14 and a pump chamber 20 is hermetically sealed by a plunger seal 52. The motor side end (rear end) 17a of the second plunger 17 is formed in such a way that a return spring 53 is supported by a spring support member 54. The rear end 17a of the plunger 17 is not separated from but is made to abut against an actuator 55 mounted on the plunger side end of the spline shaft 37 by the return spring 53 and the spring support member 54. Therefore, means for fixing the actuator 55 to the spline shaft 37 is not particularly required. An input/output signal to/from the actuator 55 is taken out to the outside of the pump body 11 from the hollow space 39 formed in the spline shaft 37.

The actuator 55 is not limited in type if it can generate a minute displacement and, for example, an actuator using a piezoelectric device or an actuator of magnetostriction type can be employed.

The construction around the first plunger 16 is the same as the construction around the second plunger 17 except for a point that the actuator 55 is mounted, so that its description will be omitted here. In the following description of operation, the second plunger 17 will be described by way of an example.

The rotational motion of the motor 31 is transmitted to the ball screw 34 by the coupling 32 and the nut 35 of the ball screw 34 and the coupling 36 drive the spline shaft 37 to realize the reciprocating linear motion of the second plunger 17. When the spline shaft 37 moves forward or backward, the second plunger 17 comes into or out of the second cylinder 14 and when the second plunger 17 comes into the second cylinder 14, it pushes out liquid to discharge the liquid into the discharge piping 5.

Hereafter, in this embodiment, a section including the first plunger 16 and a direct-acting mechanism for driving the first plunger 16 is referred to as "a large pump" and a section including the second plunger 17 and a direct-acting mechanism for driving the second plunger 17 is referred to as "a small pump".

Next, FIG. 3 is a chart to show the flow rate range of the pump for liquid chromatography and its classification. In this embodiment, a pump for liquid chromatography that feeds liquid at an extremely small flow rate of a semi-micron liter or less such as micron liter ($\mu$L) and nano liter (nL) is an object. As can be seen from one example of the flow rate range of a general-purpose pump shown in FIG. 3, the ratio of a maximum flow rate to a minimum flow rate is usually about 100 at most because of limitations of the number of revolutions and the rotational accuracy of the motor. Hence, when the flow rate is set in a micron- or nano-flow rate range, a maximum flow rate naturally becomes small. For this reason, there are presented a problem that it takes much time to fill eluate into the passage in the measurement system on the downstream side of the pump at the startup of test and a problem that bubbles remaining in the pump can not be easily discharged. In particular, when the bubbles remain in a pump chamber, there is presented a problem that even if the plunger reciprocates, it only compresses or expands the bubbles and can not discharge the smallest flow or discharges an extremely small flow, which makes it impossible to perform measurement with high accuracy.

Therefore, this embodiment is so constructed as to feed liquid at an extremely low flow rate by the small pump including the part of the second plunger and to fill the eluate into the passage and to discharge the bubbles from the pump by the large pump including the part of the first plunger at the startup of test.

Here, the total flow rate of liquid shown on a horizontal axis in FIG. 3 means the total flow rate of liquid at the time of a high-pressure gradient operation, which will be described later. In the gradient operation, the flow rate is varied in about from several tens to one hundred steps and hence a minimum flow rate of a minimum resolution to be provided by the pump becomes smaller than this by one digit or two digit.

As shown in construction examples 1, 2 in FIG. 3, the flow rate range of the small pump is set so as to cover a micron-region or a nano-region, whereas the flow rate range of the large pump is set in a larger flow rate region than this, whereby a maximum flow rate is made to reach a general-purpose region and a minimum flow rate is made smaller than the maximum flow rate of the small pump. That is, the flow rate regions of both pumps are made to overlap each other. Here, since the flow rate is a product of the sectional area of the plunger and a speed thereof, the flow rate can be variably set by varying the diameter of the plunger and the rotational speed of the motor.

Next, the feed accuracy of the plunger that determines the minimum flow rate of the small pump in the respective construction examples will be described. As described above, the minimum flow rate is determined by the sectional area of the plunger and the speed thereof. Hence, when the diameter of the plunger is determined, the flow rate is determined by the speed of the plunger, that is, the feed accuracy of the plunger. To hold the minimum flow rate of the small pump in the construction example 1, the feed accuracy of the plunger is sufficiently satisfied by the feed accuracy of the ball screw of the direct-acting mechanism. In this regard, the lead error of a commercially available precision ball screw is usually about several tens $\mu m$.

To cover the nano-region of the construction example 2, the feed accuracy of the ball screw is not sufficient and higher feed accuracy is required. Hence, in this embodiment, it is intended to achieve higher feed accuracy by employing the micro-displacement of a piezoelectric device or the like as the feed mechanism of the plunger. For example, there is a piezoelectric device that produces a displacement of several tens nm when a voltage of from 20 to 30 V is applied to the piezoelectric device, so that the amount of displacement of the piezoelectric device, that is, the stroke of the plunger can be controlled by controlling the voltage applied to the piezoelectric device. By this method, a minimum flow rate in this region can be compensated.

In the above construction, by use of FIG. 1, FIG. 2, and FIG. 4, a method for operating the pump for liquid chromatography in accordance with the invention. In FIG. 4, from the top, the displacement of the first plunger 16, the displacement of the second plunger 17, pressure at a pressure sensor 70, the flow rate of the large pump, the flow rate of the small pump, and the total flow rate passing through the discharge piping 5 are shown with respect to time on a horizontal axis.

First, when the bubbles in the pump are discharged and the eluate is filled as a preliminary stage of test, the drain valve 9 is opened and the first plunger 16 is reciprocated at a high speed to feed liquid at a large flow rate. At this time, since the large pump is arranged on the upstream side, bubbles remaining in the second pump chamber on the downstream side can be easily discharged. With this, preparation for test can be completed in the same short time as in the general-purpose pump for liquid chromatography. In this regard, the second plunger 3 is at rest during this period and the flow rate is intermittent as shown in the chart but a pulsating flow rate in this mode does not affect measurement accuracy and hence presents no problem.

Next, when the operation goes into a normal operation, the drain valve 9 is closed and the second plunger 17 is pushed into the second pump chamber 20 at a low speed to feed the liquid at a low flow rate. During this period, the first plunger 16 is basically at rest and only the small pump feeds the liquid. Next, when the second plunger 17 reaches near full stroke, it is pulled back at maximum high speed and the first plunger 16 is pushed into the first pump chamber in synchronization with the retraction to cancel the pulsation of the flow rate. In this manner, the first plunger 16 and the second plunger 17 are controlled in such a way as to keep the total flow rate at all times at a constant flow rate. That is, if the sum of absolute values of Q1 and Q2 in the chart is made equal to Q3, the liquid can be always fed at a constant flow rate. In FIG. 3, the reason why the flow rate range of the large pump overlaps the flow rate range of the small pump is to cancel the respective flow rates to eliminate pulsation in the flow rate. The larger the maximum flow rate of the large pump, the larger the effect. However, since there is a limitation that the minimum flow rate needs to be equal to the sum of absolute values of Q1 and Q2, the maximum flow rate naturally is also limited. Hence, if the second plunger is pulled back as quickly as possible to increase Q2, the minimum flow rate of the large pump can be increased and at the same time the maximum flow rate can be also increased.

In this regard, while the second plunger 17 is pushed into the second pump chamber 20, the first plunger 16 is basically at rest and only the small pump produces flow rate but a method for displacing the first plunger 16 by Xini, as shown in the chart, when pressure is increased to a predetermined value Pset at the startup is effective. To increase the pressure to the predetermined value, the plunger needs to be pushed into the pressure chamber to a certain degree because of the compressibility of fluid and the deformation of seals, but it is said that increasing pressure at the startup is more effectively performed by the large pump.

In the above method of operating a pump, in the construction example 1, a method for driving the plunger is performed by a direct-acting mechanism such as ball screws by the rotational motion of the motor or the like. In contrast to this, in the construction example 2, the method for driving the plunger is performed by driving an actuator. However, in the construction example 2 is also thought a method for driving the actuator in cooperation with a method for driving the direct-acting mechanism by the motor.

Incidentally, in FIG. 1 is shown a case where the diameter of the first plunger of the large pump is equal to the diameter of the second plunger of the small pump. However, the invention is not limited to this construction but a construction may be employed in which the diameter of the first plunger is larger than the diameter of the second plunger.

Moreover, in the present embodiment, a method for converting the rotational motion of the motor to direct-acting mechanism has been disclosed as means for driving the plunger. However, the invention is not limited to this but a construction may be employed in which the plunger is driven, for example, by a linear motor.

Another feature of the present embodiment lies in that the actuator 55 is used as a load sensor for a load applied to the plunger when it does not function as an actuator. In other words, in the construction example 1, in a case where the plunger is driven by the direct-acting mechanism such as ball screws by the rotation of the motor, the actuator 55 is not used and hence is utilized as a load sensor as alternative means of a pressure sensor because there is correlation between load applied to the plunger and pressure applied to the plunger by use of the relationship between voltage and displacement. If the amount of strain (amount of displacement) with respect to pressure and the relationship between voltage and the amount of strain are quantitatively grasped, by measuring outputted voltage, pressure at that time can be acquired. The signal outputted to the controller 60 from the actuator 55 shown in FIG. 1 and FIG. 2 shows the above-described construction.

Therefore, this construction example can produce an effect of eliminating the need for providing a pressure sensor.

Figure 5:
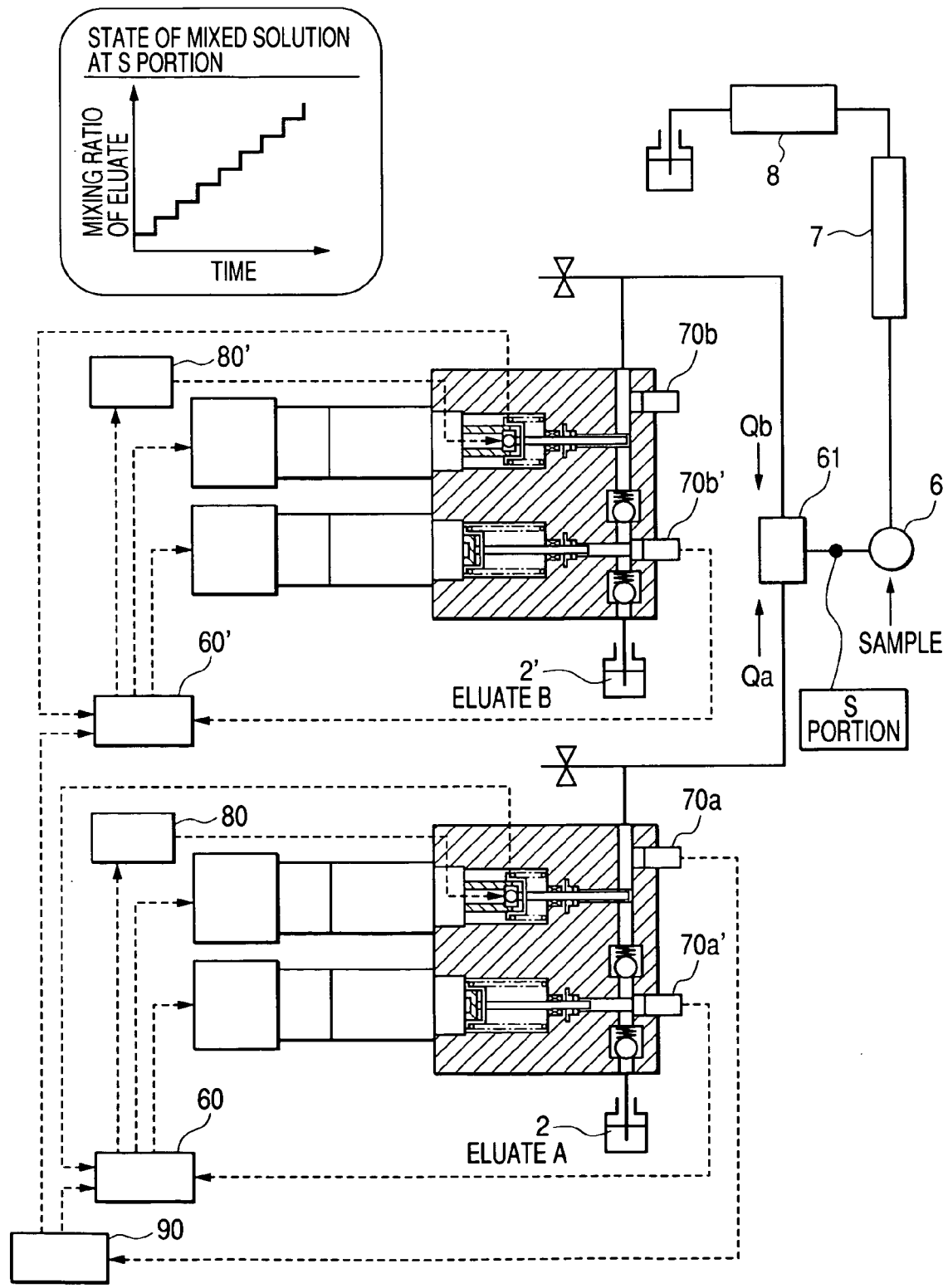
FIG. 5 is an illustration to show one example of a system construction using the pump for liquid chromatography of the invention.

Next, FIG. 5 shows an example in which two pumps for liquid chromatography in accordance with the invention are used to construct a high-pressure gradient system. A gradient operation means a method for varying the mixing ratio of two kinds of eluates A, B stepwise with the passage of time and test is conducted by varying the ratio of Qa to Qb while keeping the total amount of flow rate of liquid (=Qa+Qb) at the same amount.

Figure 6:
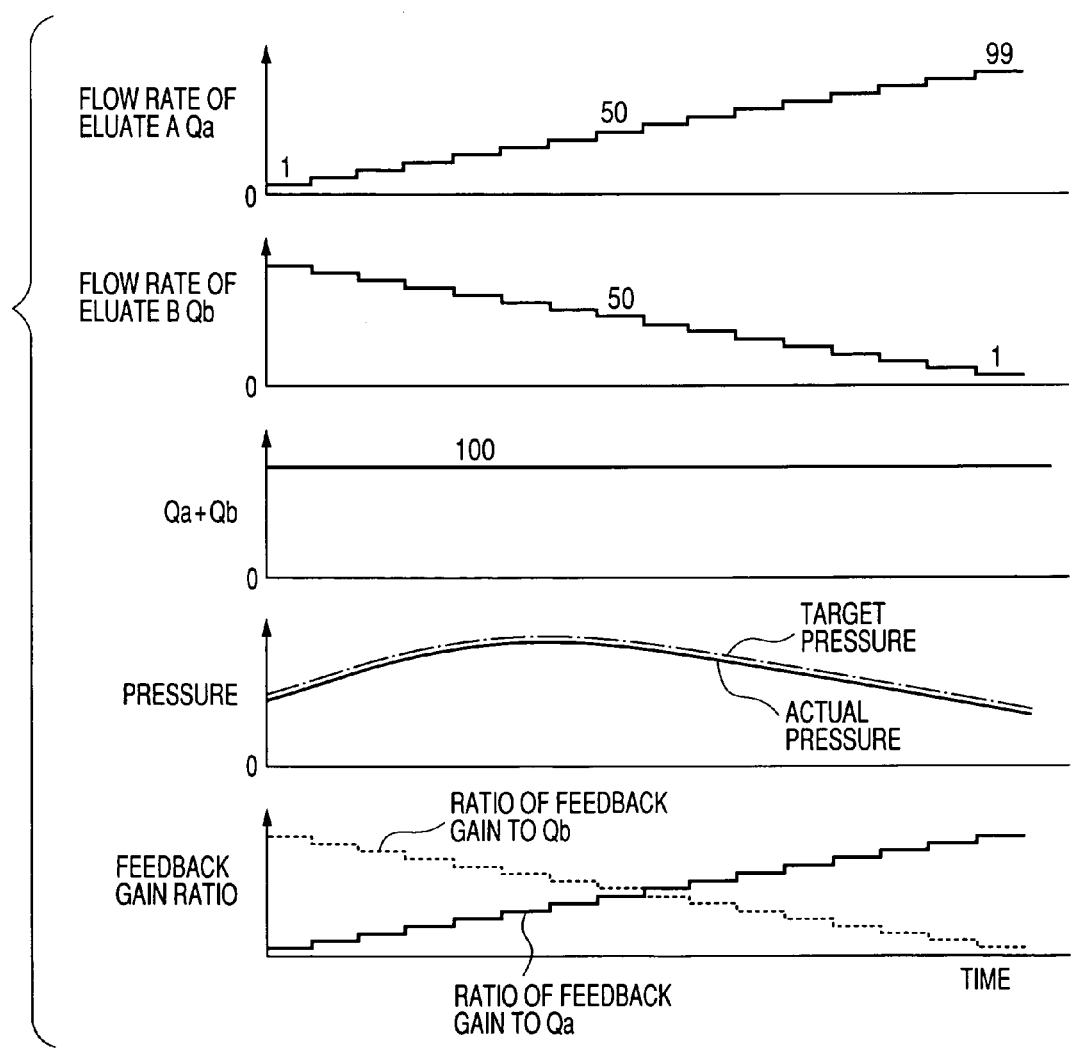
FIG. 6 is a chart to show one example of a method for driving the pump for liquid chromatography of the invention.

FIG. 6 shows that the respective elements vary with time in the gradient operation. Assuming that (Qa+Qb) is kept at a constant value of 100, at first, the mixing ratio is started from Qa:Qb=1:99 and then is sequentially changed to 2:98, 3:97, . . . , 50:50, . . . , and 99:1. This shows a case where the mixing ratio is changed by 100 steps and assuming that the total amount of flow rate of liquid is 1 μL/min, a minimum flow rate and resolution of flow rate need to be 1/100 of this value, that is, 10 nL/min. It has been known that as shown in the charts in FIG. 6, even if the liquid is flowed at a constant flow rate, the composition of the fluid is varied by the mixing ratio, so that fluid resistance when the liquid passes through the column is varied to vary the discharge pressure of the pump by about 1.5 to 2 times at the maximum. For this reason, when it is intended to keep the pressure at a constant value, on the contrary, the flow rate is varied.

On the other hand, since the relationship between the mixing ratio and pressure variation is previously known from past experimental data, a pressure variation curve in a case where the flow rate is constant can be predicted. Hence, if the theoretical value of this pressure variation curve is a target pressure and a pressure sensor signal is fed back to drive the pump to match an actual pressure with the target pressure, a constant total flow rate of liquid can be acquired with high accuracy. To be specific, the signal of the pressure sensor 70a in FIG. 5 is fed back to the main controller 90 to control the controllers 60, 60' of the respective pumps to make the pressure follow the target pressure. In this respect, since the discharge passages of both pumps communicate with each other via a mixer 61, the pressure is almost equal at any portions and hence any one of the pressure sensors 70a, 70b can be used.

If the actual pressure is lower than the target pressure, the total flow rate of liquid (=Qa+Qb) is decreased and hence the number of revolutions of the motor needs to be increased to increase the flow rate. However, it can not be determined from the information of one pressure sensor which of Qa and Qb is decreased. If it is determined that Qb is decreased and Qb is corrected in spite of the fact that Qa is actually decreased, on the contrary, the accuracy of the mixing ratio deteriorates. This is a problem that is called a mutual interference in the gradient motion.

To avoid this mutual interference, in this embodiment, Qa and Qb are corrected on the assumption that Qa and Qb are decreased at the same rate. This can be realized by providing feedback gains proportional to a flow rate ratio as shown in the chart in FIG. 6. For example, the feedback gains of Qa and Qb in a case where the pump is operated at a flow rate ratio (Qa:Qb) of (20:80) are given as (20/100)×K, (80/100)×K, respectively, where K is a constant. If the total flow rate of liquid is 5 short and a proportional control is performed, command values of Qa and Qb are given as 20+(20/100)×K×5 and 80+(80/100)×K×5, respectively. For example, assuming that K is 1, the former command value becomes 21 and the latter command value becomes 84. According to this method, although a decrease in the mixing accuracy caused by the individual difference between the two pumps cannot be avoided, the problem of mutual interference can be avoided and hence a further decrease in the mixing accuracy can be prevented.

In this regard, since the discharge pressure varies with time, the pressures in the pump chambers of both pumps need to be varied in accordance with the varying discharge pressure. In particular, in a case where pressure at the pressure sensor is lower than pressure in the pump chamber of the first pump, the discharge valve is opened, whereby the eluate in the first pump chamber flows into the second pump chamber to increase the flow rate of liquid. For this reason, in this embodiment, the pressure sensor is provided in the first pump chamber of each of both pumps and the signal of the pressure sensor is fed back to the controller to drive the first plunger to thereby control the first plunger in such a way that the pressure in the first pump chamber is equal to the discharge pressure measured by the pressure sensor.

In the manner described above, there can be provided a high-pressure gradient system excellent in stable liquid feed and in mixing accuracy.

Figure 7:
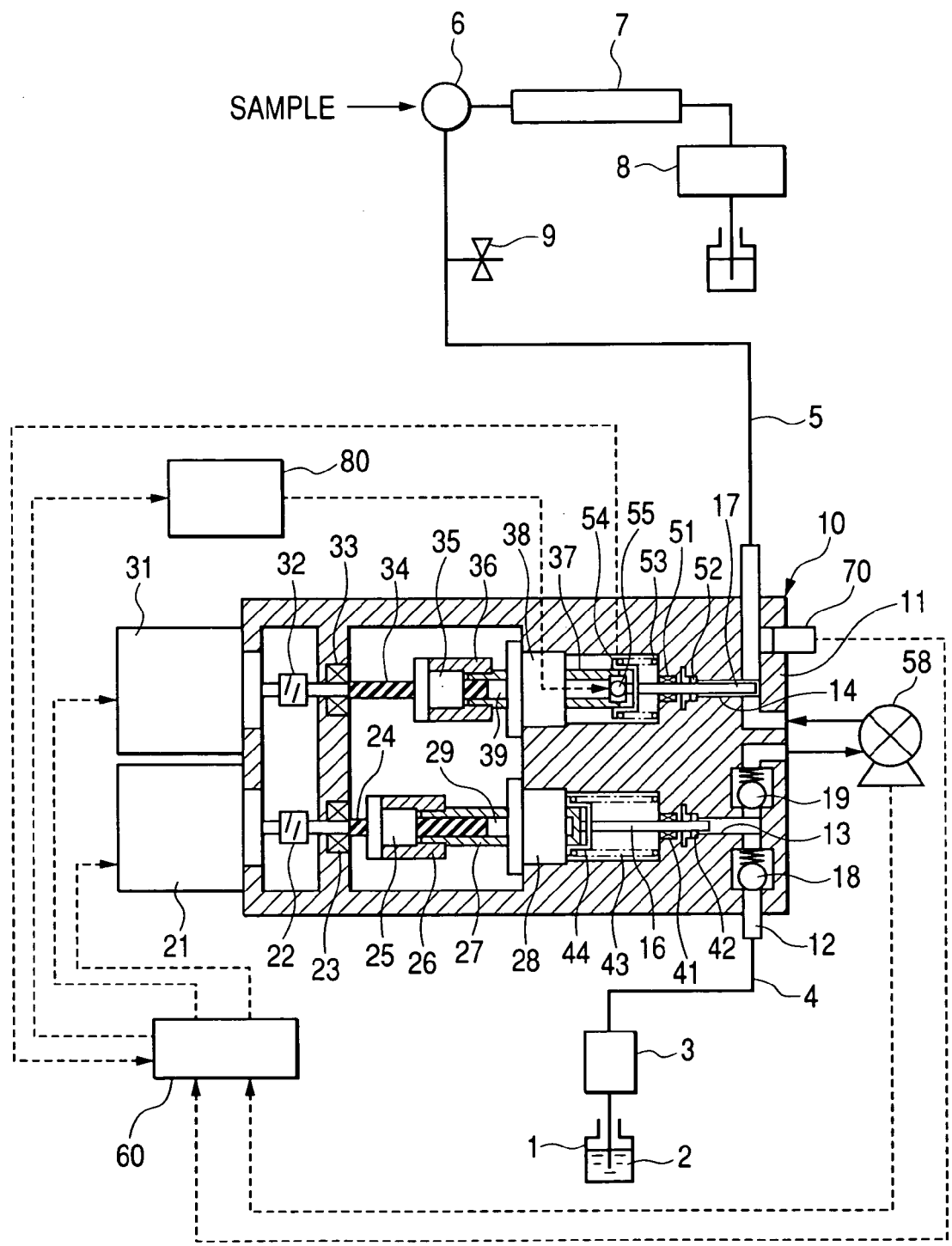
FIG. 7 is a hydraulic circuit to show the general construction of a system for feeding liquid as an example of another object to which a pump for liquid chromatography of the invention is applied.

FIG. 7 is another embodiment of a pump for liquid chromatography of the invention. The parts equivalent to those of the pump for liquid chromatography shown in FIG. 1 will be denoted by the same reference symbols and their descriptions will be omitted. This embodiment is characterized by the construction in which an active valve 58 is interposed between the discharge valve 19 and the second pump chamber and is controlled by the controller 60.

In general, a suction valve and a discharge valve used for a pump for a liquid chromatography are so-called check valves and a material of high hardness such as stainless steel, ruby, or ceramics is used as the material of balls from the viewpoint of chemical resistance and durability. In the check valve of this kind, a minute leakage cannot be avoided even in a state where the check valve is closed and becomes a large factor to reduce a liquid feed accuracy, in particular, in the case of feeding liquid at an extremely low flow rate.

The present pump has a construction in which the liquid is fed at a low flow rate by the second plunger 17. As the present pump is thought a syringe pump of one stroke type in which measurement is finished when the second plunger 17 reaches its full stroke.

Figure 8:
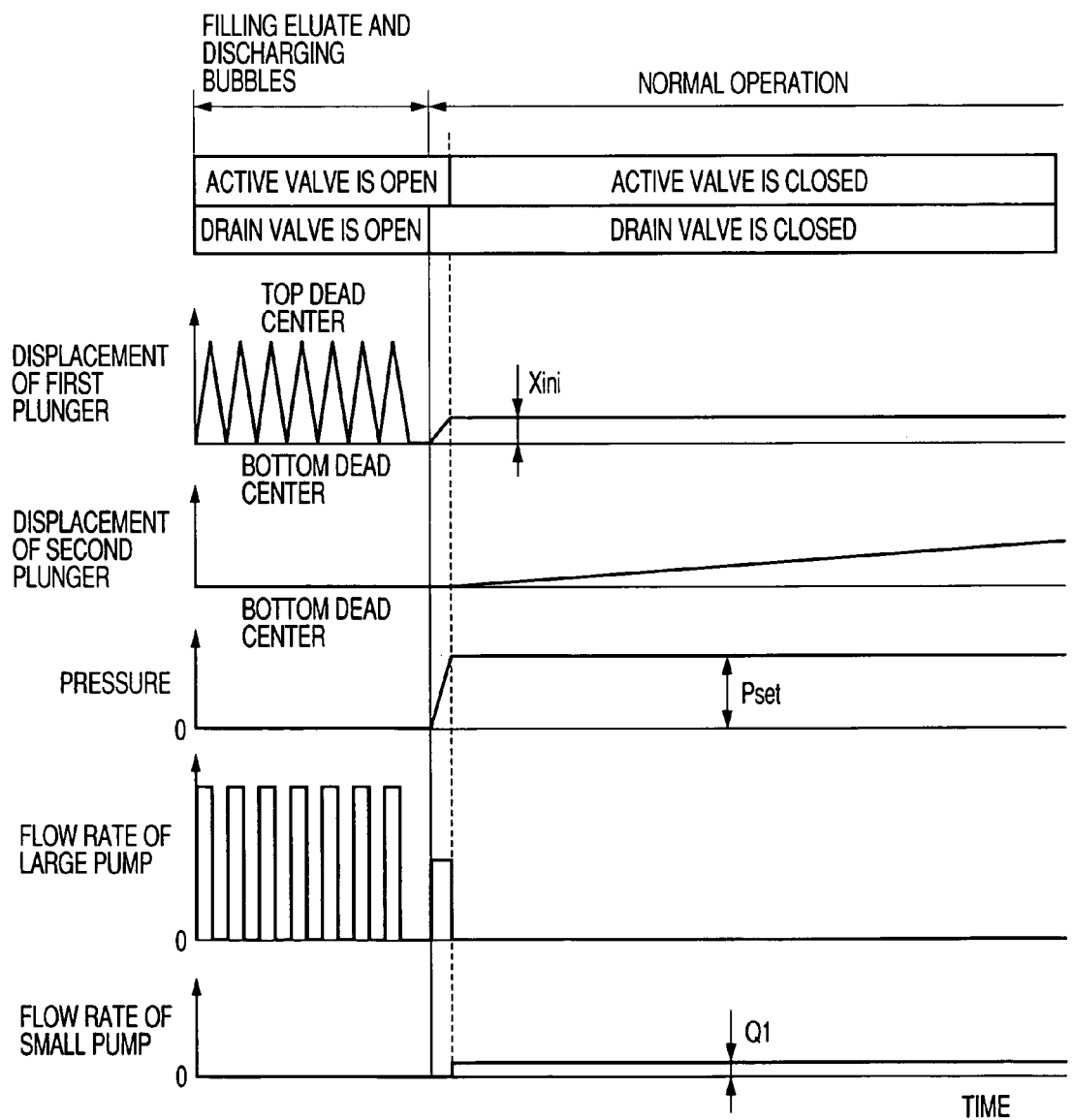
FIG. 8 is a chart to show one example of a method for driving liquid chromatography of the invention.

In FIG. 8 is shown one example of a method for operating the present pump. At first, both of the active valve 58 and the drain valve 9 are opened and the first plunger 16 is reciprocated at a high speed to feed liquid at a large flow rate to thereby fill eluate into the pump while discharging bubbles in the pump. At this time, since the large pump is arranged on the upstream side, the bubbles remaining in the second pump chamber on the downstream side can be easily discharged. With this, preparation for test can be completed in the same short time as in the general-purpose pump for liquid chromatography. Here, the second plunger 17 is at rest and the flow rate is intermittent during this period as shown in the chart in FIG. 8 but a pulsating flow rate does not affect measurement accuracy in this mode and hence presents no problem.

Next, when the operation goes into a normal operation, the drain valve 9 is closed and the first plunger 16 is displaced by Xini to increase the discharge pressure to a predetermined value Pset. After the discharge pressure is increased to the Pset, the active valve 58 is closed and the first plunger 16 is stopped and the second plunger 17 is pushed into the second pump chamber at a low speed to feed the liquid at a low flow rate of Q1.

In this construction, when the second plunger 17 is pushed to full stroke, measurement is finished and the second plunger 17 is not pulled back, so that pulsation hardly occurs inherently. Moreover, since the eluate is sealed at two positions of the active valve 58 and the discharge valve 19, leakage can be greatly reduced as compared with the check valve. Hence, this construction has a feature that the flow rate fed by the plunger can be discharged with extremely high accuracy. Here, needless to say, the driving of the second plunger 17 at this time is performed by the actuator 55.

Although the operation is finished by one stroke, the operation can be performed continuously for 24 hours in the nano-region where the total flow rate of liquid is nL/min. Therefore, it can be said that the pump for liquid chromatography in FIG. 7 is especially effective when a specification of a lower flow rate of nano-class is realized.

Moreover, in this embodiment, one pump body is provided with two pressure chambers and the pressure chambers are connected to each other by a passage. However, it is also recommended that pump heads are separately provided and connected to each other by a piping to construct a system. With this, the pump can be easily disassembled and hence maintenance work such as seal exchange can be easily performed. Moreover, an advantage of improving the ease with which the parts are laid out can be provided.

What is claimed is:

1. A pump including a cylinder and a plunger that reciprocates in the cylinder to suck and discharge liquid comprising:
    a motor;
    motion conversion means that converts a rotational motion of the motor to a reciprocating motion and drives the plunger;
    an actuator that drives the plunger by more minute displacement than the motion conversion means;
    a drive part that drives the actuator, and
    a controller that selectively switches between operation of the motor and operation of the drive part.

2. The pump according to claim 1, wherein the actuator directly drives the plunger, and the motion conversion means drives the plunger via the actuator.

3. The pump according to claim 1, wherein the actuator is formed of an actuator using a piezoelectric element or a magneto-striction type actuator that generate a minute displacement, and wherein the motion conversion means is formed of a ball spline mounted between a rotational axis of the motor and the actuator.

4. The pump for liquid chromatography as claimed in claim 1, wherein the actuator is interposed between an end portion of the motion conversion means and an end portion of the plunger, wherein the plunger comprises a return spring providing a spring force to the actuator side.

5. A pump including a cylinder and a plunger that reciprocates in the cylinder to suck and discharge liquid, comprising:
    a first pump having a first cylinder and a first plunger reciprocating in the first cylinder; and
    a second pump having a second cylinder, a second plunger reciprocating in the second cylinder, a motor, motion conversion means that converts a rotational motion of the motor to a reciprocating motion and drives the second plunger, an actuator that drives the second plunger by more minute displacement than the motion conversion means, and a drive part that drives the actuator; and
    a controller that selectively switches between operation of the first pump and operation of the second pump, and, at the same time, selectively switches, within the first pump, between operation of the motor and operation of the drive part,
    wherein, a flow rate of liquid is greater in the first pump than in the second pump.

6. The pump according to claim 5, wherein the actuator is formed of an actuator using a piezoelectric element or a magneto-striction type actuator that generate a minute displacement, and wherein the motion conversion means is formed of a ball spline mounted between a rotational axis of the motor and the actuator.

7. The pump for liquid chromatography as claimed in claim 5, wherein the actuator is interposed between an end portion of the motion conversion means and an end portion of the second plunger, wherein the second plunger comprises a return spring providing a spring force to the actuator side.

8. A pump for liquid chromatography including a cylinder and a plunger that reciprocates in the cylinder to suck and discharge liquid, comprising:
    a motor;
    motion conversion means that converts a rotational motion of the motor to a reciprocating motion and drives the plunger;
    an actuator that directly drives the plunger by more minute displacement than the motion conversion means;
    a drive part that drives the actuator; and
    a controller that selectively switches between operation of the motor and operation of the drive part.

9. The pump for liquid chromatography as claimed in claim 8, including:
    a first pump having a first cylinder and a first plunger reciprocating in the first cylinder;
    a second pump having a second cylinder and a second plunger reciprocating in the second cylinder;
    a suction valve provided on an upstream side of the first pump;
    a discharge valve provided on an downstream side of the first pump; and
    an actuator provided at least in the second plunger of the second pump, wherein the second pump is arranged on the most downstream side of the plurality of pumps constructed in the pump for liquid chromatography.

10. A pump for liquid chromatography including a cylinder and a plunger that reciprocates in the cylinder to suck and discharge liquid, comprising:
    a first pump having a first cylinder and a first plunger reciprocating in the first cylinder; and
    a second pump having a second cylinder, a second plunger reciprocating in the second cylinder, a motor, motion conversion means that converts a rotational motion of the motor to a reciprocating motion and drives the second plunger, an actuator that drives the second plunger by more minute displacement than the motion conversion means; and a drive part that drives the actuator; and a controller that selectively switches between operation of the first pump and operation of the second pump, and, at the same time, selectively switches, within the first pump, between operation of the motor and operation of the drive part, wherein, a flow rate of liquid is greater in the first pump than in the second pump.

11. The pump for liquid chromatography as claimed in claim 8 or claim 10, wherein the controller executes switching in accordance with a flow rate of liquid of the pump.

12. The pump for liquid chromatography as claimed in any one of claims 8 to 10, wherein the actuator also serves as a sensor for detecting a load applied to the plunger.

13. The pump for liquid chromatography as claimed in claim 8 or claim 10, wherein a flow rate of liquid ranges about from 0.1 nL/min to 50 μL/min.

14. The pump for liquid chromatography as claimed in claim 10, further comprising a drain valve provided on a downstream side of the second pump, wherein when a test is started, the drain valve is opened and the first pump feeds liquid at a large flow rate to discharge bubbles remaining in a passage and at the same time fills the liquid into a downstream passage, and wherein the drain valve is then closed and the second pump feeds the liquid at a low flow rate.

15. The pump for liquid chromatography as claimed in claim 10, further comprising a discharge valve provided on a downstream side of the first pump and an active valve provided between the discharge valve and the second pump.

* * * * *